(12) United States Patent
Huang et al.

(10) Patent No.: US 10,139,608 B2
(45) Date of Patent: Nov. 27, 2018

(54) SELECTIVE PLANE ILLUMINATION MICROSCOPY (SPIM) SYSTEMS AND METHODS

(71) Applicant: THE REGENTS OF THE UNIVERSITY OF CALIFORNIA, Oakland, CA (US)

(72) Inventors: Bo Huang, San Francisco, CA (US); Ryan McGorty, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/516,620

(22) PCT Filed: Oct. 2, 2015

(86) PCT No.: PCT/US2015/053656
§ 371 (c)(1),
(2) Date: Apr. 3, 2017

(87) PCT Pub. No.: WO2016/054474
PCT Pub. Date: Apr. 7, 2016

(65) Prior Publication Data
US 2017/0293130 A1 Oct. 12, 2017

Related U.S. Application Data

(60) Provisional application No. 62/058,882, filed on Oct. 2, 2014.

(51) Int. Cl.
*G02B 5/06* (2006.01)
*G02B 21/00* (2006.01)
(Continued)

(52) U.S. Cl.
CPC ........ *G02B 21/0088* (2013.01); *B01L 3/5027* (2013.01); *G01N 21/6458* (2013.01);
(Continued)

(58) Field of Classification Search
CPC .... G02B 21/0088; G02B 21/04; G02B 21/06; G02B 21/16; G02B 21/24; G02B 21/362; G02B 21/367
(Continued)

(56) References Cited

U.S. PATENT DOCUMENTS 4,717,239 A * 1/1988 Steenblik ................. G02B 5/04
348/E13.033
4,953,956 A 9/1990 Carpenter
(Continued)

FOREIGN PATENT DOCUMENTS

WO 2014005682 A3 1/2014
WO 2014180884 A1 11/2014
(Continued)

OTHER PUBLICATIONS

International Search Report for PCT/US2015/053656 dated Dec. 29, 2015.
(Continued)

*Primary Examiner* — Euncha Cherry
(74) *Attorney, Agent, or Firm* — Thomas | Horstemeyer, LLP

(57) ABSTRACT

In one embodiment, a selective plane illumination microscopy system for capturing light emitted by an illuminated specimen includes a specimen stage having a top surface adapted to support a specimen holder and an opening adapted to provide access to a bottom of the holder, and a selective plane illumination microscopy optical system positioned beneath the stage, the optical system including an excitation objective, a detection objective, and an open-top, hollow prism that is adapted to contain a liquid, wherein the prism is positioned within the opening of the stage and optical axes of the objectives are aligned with the prism such
(Continued)

that the axes pass through the prism and intersect at a position near the top surface of the specimen stage.

19 Claims, 8 Drawing Sheets

(51) Int. Cl.
  G02B 21/16   (2006.01)
  G02B 21/24   (2006.01)
  G02B 21/36   (2006.01)
  G02B 21/04   (2006.01)
  G02B 21/06   (2006.01)
  B01L 3/00    (2006.01)
  G01N 21/64   (2006.01)

(52) U.S. Cl.
  CPC .............. *G02B 5/06* (2013.01); *G02B 21/04* (2013.01); *G02B 21/06* (2013.01); *G02B 21/16* (2013.01); *G02B 21/24* (2013.01); *G02B 21/362* (2013.01); *G02B 21/367* (2013.01); *G01N 21/6452* (2013.01)

(58) Field of Classification Search
  USPC .................................................. 359/363, 832
  See application file for complete search history.

(56) References Cited

U.S. PATENT DOCUMENTS

| | | | | |
|---|---|---|---|---|
| 5,982,534 | A * | 11/1999 | Pinkel | G01N 21/6458 359/387 |
| 8,570,649 | B2 | 10/2013 | Truong | |
| 8,575,570 | B2 | 11/2013 | Choi | |
| 2005/0264877 | A1 | 12/2005 | Mandella et al. | |
| 2009/0174937 | A1* | 7/2009 | Holy | G02B 21/08 359/382 |
| 2009/0231689 | A1* | 9/2009 | Pittsyn | G01B 9/04 359/363 |
| 2009/0237765 | A1 | 9/2009 | Lippert | |
| 2011/0115898 | A1 | 5/2011 | Hikosaka | |
| 2012/0099190 | A1 | 4/2012 | Knebel | |
| 2013/0100272 | A1* | 4/2013 | Price | G02B 7/38 348/79 |
| 2014/0099659 | A1 | 4/2014 | Keller | |
| 2016/0139394 | A1 | 5/2016 | Taniguchi | |

FOREIGN PATENT DOCUMENTS

| | | |
|---|---|---|
| WO | 2015004107 A1 | 1/2015 |
| WO | 2015036589 A1 | 3/2015 |

OTHER PUBLICATIONS

Huisken, et al., "Selective plane illumination microscopy techniques in developmental biology", Dept of biochemistry and biophysics, and cardiovascular research institute, development, 2009.
Huisken, et al., "Optical sectioning deep inside live embryos by selective plane illumination microscopy", Science, vol. 305, Aug. 2004.
Santi, Peter, "Light Sheet Fluorescence Microscopy: A Review", J. Histochem Cytochem, Sage publications, 2011.
Wu, et al., "Inverted selective plane illumination microscopy (iSPIM) enables coupled cell identity lineaging and neurodevelopmental imaging in Caenorhabditis elegans", National Institute of Biomedical Imaging and Bioengineering, Sep. 2011.
Smith, Caitlin, "Image embryos in action in light-sheet microscopy", Biocompare, Apr. 2014.
Zeiss, Carl, "Light sheet microscopy system", BioOptics World, Oct. 2012.
Tomer, et al., "Quantitative high-speed imaging of entire developing embryos with simultaneous multi-view light sheet microscopy", Nature Methods, 2012.
Dodt, et al., "Ultramicroscopy: three-dimenstional visulization of neuronal networks in the whole mouse brain", Nat Methods, 4, 331-336, 2007.
Huisken, et al., "Optical sectioning deep inside live embryos selective plane illumination microscopy", Science Mag, vol. 305, Aug. 13, 2004.
Huisken, et al., "Selective Plan Illumination Microscopy Techniques in Developmental Biology", Development, 136, 1963-1975, 2009.
Tomer, et al. "Shedding light on the system: Studying embryonic development with light sheet microscopy", Science Direct, Genetics and Development, Corr Opin Genet Dev 21, 558-565, 2011.
Holekamp, et al., "Fast Three-Dimensional Fluorescence Imaging of Activity in Neural Populatiosn by objective-coupled planar illumination microscopy", Neuron Neurotechnique, Cel Press, 57, 661-272, 2008.
Cutrale, et al., "Inclined selective plane illumination microscopy adaptor for conventional microscopes", Microscopy Research and Technique 76: 1461-1466, 2012.
Tokunaga, et al., "Highly inclined think illumination enables clear signle-molecule imaging in cells", Nat. Methods, 5, 159-161, 2008.
Gebhardt, et al., "Signle-molecule imaging of transcription factor binding to DNA in live mammalian cells", Nat Methods 10, 421-426, 2013.
Vladimirov, N., "Light-sheet functional imaging in fictively behaving zebrafish", Nat. Methods, 2014.
Keller, et al., "Fast, high-contrast imaging of animal development with scanned light sheet-based structured-illumination microscopy", Nature America, Inc., 322, 1065-1069, 2008.
Keller, et al., "Reconstruction of Zebrafish early embryonic developement by scanned light sheet microscopy", Science Mag.Org, vol. 322, Nov. 2008.
Wu, et al., "Spatially isotropic four-dimensional imaging with dual-view plane illumination microscopy", Nature biotechnologyProc. Natl Acad Sci, 108, 17708-17713, 2011.
Planchon, et al., "Rapid three-dimensional istropic imaging of living cells using Bessel beam plant illumination", Nat. Methods 8, 417-423, 2011.
Rand, et al., "Methylmercury disruption of embryonic neural development in drosophila", NeuroToxicology 30, 794-802, 2009.
Li Jeon, et al., "Generation of Solution and Surface Gradients Using Microfluidic Systems", Langmuir 16, 8311-8316, 2000.
Schindelin, et al., "Fiji: an open-source platform for biological-image analysis", Nat. Methods, 9, 676-682, 2012.
Wu, et al., "Inverted selective plane illumination microscopy (iSPIM) enables coupled cell identity lineaging and neurodevelopmental imaging in the Caenorhabditis elegans", Nat. Biotechnol, 31, 1032-1038. 2013.
European Search Report for Application No. 15846370.3-1020 / 3201672 dated Apr. 25, 2018.

* cited by examiner

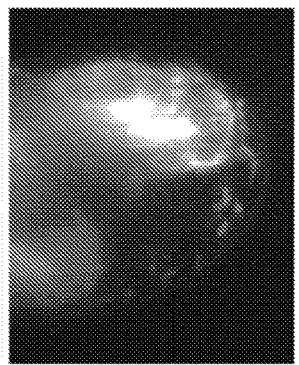
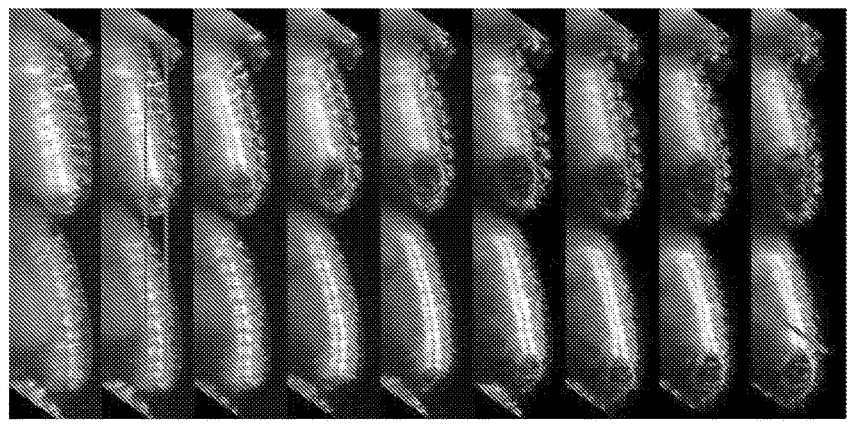
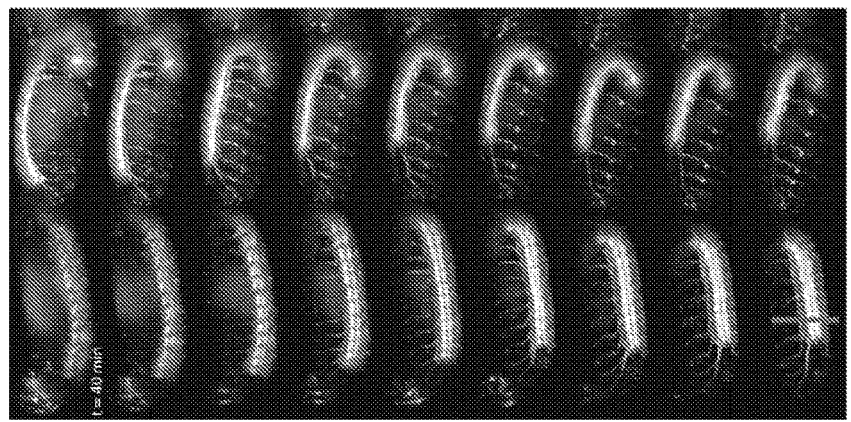
FIG. 5(a) FIG. 5(b) FIG. 5(c) FIG. 5(d) FIG. 5(e) FIG. 5(f)

FIG. 7(a)
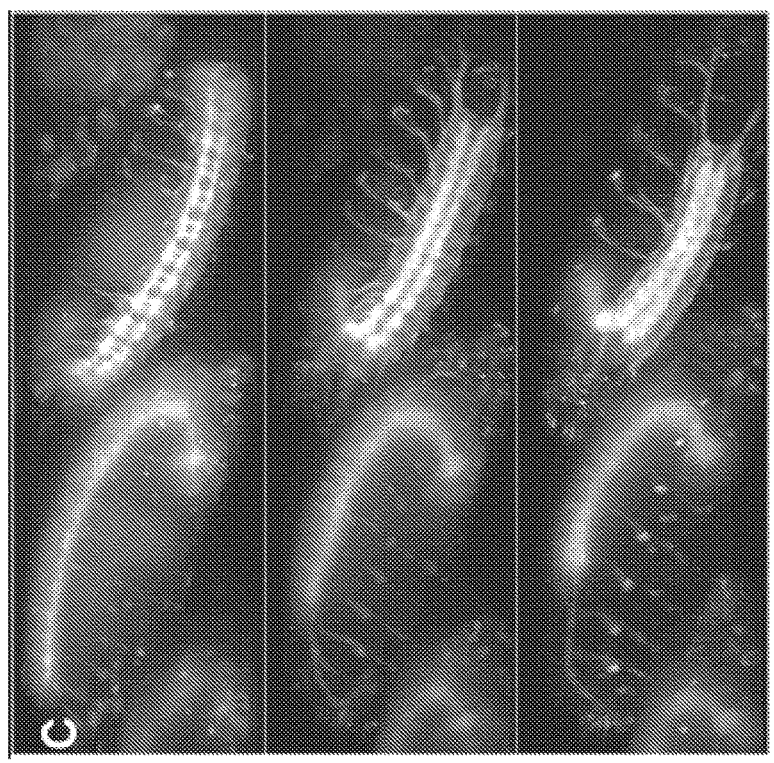
FIG. 7(b)
FIG. 7(c)
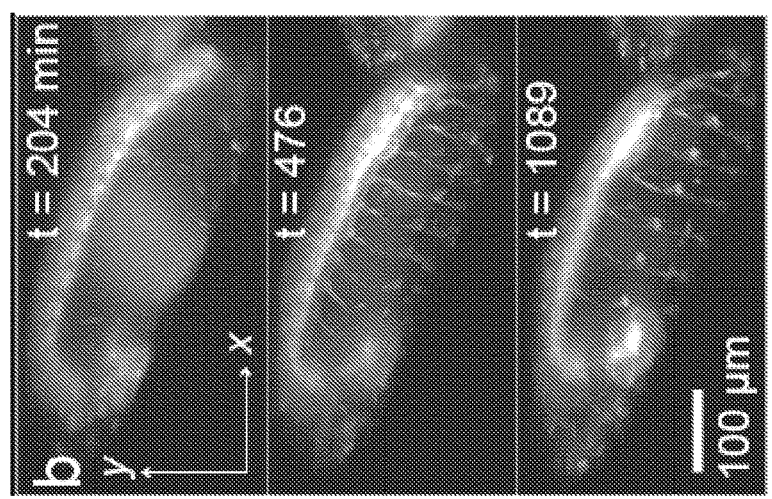
FIG. 7(d)

FIG. 7(e)
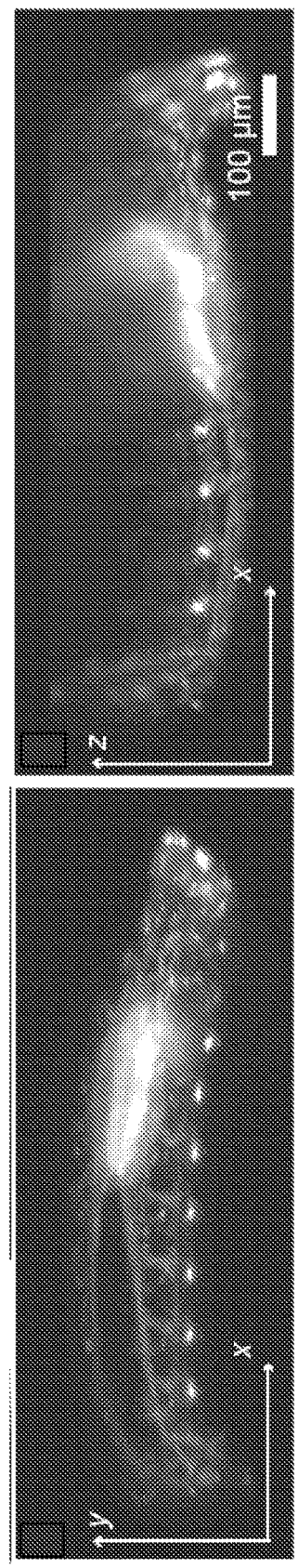
FIG. 7(f)
FIG. 7(g)

SELECTIVE PLANE ILLUMINATION MICROSCOPY (SPIM) SYSTEMS AND METHODS

CROSS-REFERENCE TO RELATED APPLICATION

This application is the 35 U.S.C. § 371 national stage application of PCT Application No. PCT/US2015/053656, filed Oct. 2, 2015, where the PCT claims priority to U.S. Provisional Application Ser. No. 62/058,882, filed Oct. 2, 2014, both of which are hereby incorporated by reference in their entireties.

NOTICE OF GOVERNMENT-SPONSORED RESEARCH

This invention was made with Government support under grant numbers R21 NS082938 and R33 EB019784, awarded by the National Institutes of Health (NIH). The Government has certain rights in the invention.

BACKGROUND

Visualizing the development or response to stimuli of live, whole organisms at cellular resolution with fluorescence microscopy is critical in answering key biological questions. Over the last few years, selective plane illumination microscopy (SPIM) has emerged as an optical sectioning technique particularly well-suited for volumetric fluorescence imaging of whole organisms over an extended period of time with high temporal resolution. In SPIM, a sheet of excitation light passes through the specimen and is coincident with the focal plane of a detection objective. Scanning this light sheet in synch with the focal plane of the detection objective relative to the specimen provides volumetric imaging wherein portions of the specimen not in the focal plane receive no excitation light. Therefore, limited phototoxicity and photobleaching occur as compared to confocal or wide-field imaging methods.

In a common implementation of SPIM, the illumination and detection objectives are placed orthogonally on two sides of a liquid-filled chamber above a platform on which the chamber is placed. The specimen is held within a cylinder of gel that is vertically positioned within the chamber and that can be rotated and/or translated. Both objectives focus on the specimen either through glass windows on the sides of the chamber or with water-dipping objectives that enter the chamber. Other arrangements for SPIM enable the use of horizontally mounted specimens. In such cases, the illumination and detection optical axes are positioned above the platform and water-dipping objectives are immersed into the specimen chamber from above.

Although the above-described SPIM systems are compatible with some conventional specimen mounting protocols, they do not enable the use of commercially available multiwell plates or specimens held within microfluidic chambers. Furthermore, the benefits of using inverted microscopes, such as having easy access to the specimen from above and being able to quickly exchange specimens without adjusting the optics, are unavailable with these setups. It can therefore be appreciated that it would be desirable to have a SPIM system and method that enable the use of conventional specimen holders and possesses the benefits of inverted microscopy.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 5 comprises images of developing Drosophila embryos captured using the microfluidic device of FIG. 4. FIG. 5(a) shows the z-projection of 32 Drosophila embryos that have been loaded into an approximately 14 mm section of a microfluidic channel of the device. Only every 10th frame was used to generate the figure. FIG. 5(b) shows the two embryos in the red box in FIG. 5(a) are shown at different times. The images again display z-projections but all frames acquired were used. FIG. 5(c) shows the same embryos and same time points as FIG. 5(b) are shown as y-projections. FIG. 5(d) shows two slices in the x-y plane are shown corresponding to the red lines in FIG. 5(c). FIG. 5(e) shows an image of embryo as acquired by the camera and corresponding to the position indicated by the red lines in the last time point in FIGS. 5(b) and 5(c). FIG. 5(f) shows a z-projection like that in FIG. 5(a) but 650 minutes later.

FIG. 7 comprises images of developing and moving Drosophila captured using the microfluidic device of FIG. 6. FIG. 7(a) shows a z-projection of 32 Drosophila embryos loaded into a straight microfluidic channel of the device along which a decreasing gradient in methylmercury chloride runs from left to right. Only every 6th frame recorded was used to generate this image. FIG. 7(b) shows the embryos in the left box in FIG. 7(a) at different time points. The images again display z-projections but all frames acquired were used. FIG. 7(c) shows the z-projections of the embryo in the right box at the same times points as FIG. 7(b). FIG. 7(d) shows a similar z-projection of the entire row of embryos as FIG. 7(a) but at a later time point. FIG. 7(e) shows z-projections of four moving first instar larvae at different time points. FIG. 7(f) shows a z-projection of the larva highlighted. FIG. 7(g) shows a y-projection of the same larva shown in FIG. 7(f).

FIG. 9 comprises images of zebrafish contained in 96-well plates.

DETAILED DESCRIPTION

As described above, it would be desirable to have a selective plane illumination microscopy (SPIM) system and method that enable the use of conventional specimen holders and possesses the benefits of inverted microscopy. Disclosed herein are examples of such SPIM systems and methods. In some embodiments, a SPIM system comprises an optical system including an excitation objective and a detection objective that are both positioned beneath a stage on which a specimen holder is supported. The optical system further includes an open-top, hollow prism that contains a liquid, such as water, that contacts the bottom surface of the specimen holder. The specimen can be imaged through the prism. In some cases, the objectives are air objectives that do not contact the liquid. In other embodiments, the objectives are dipping objectives that are immersed in the liquid.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
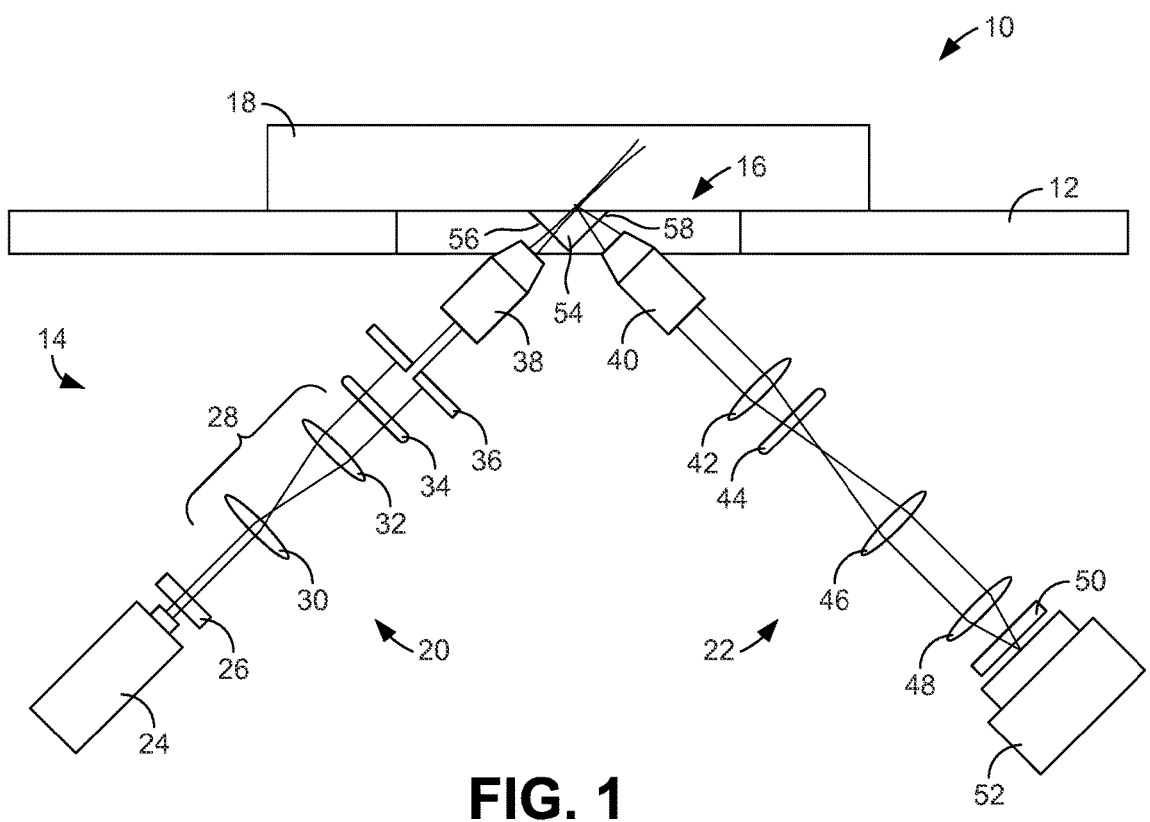
FIG. 1 is a schematic side view of a first embodiment of a selective plane illumination microscopy (SPIM) system.

FIG. 1 illustrates an embodiment of a SPIM system that is adapted for use with conventional specimen holders, such as petri dishes, multiwell plates, and microfluidic chambers. The system comprises a SPIM microscope 10 that includes a motorized stage 12, in the form of a horizontal platform, and a SPIM optical system 14 that is positioned beneath the stage. As shown in FIG. 1, the stage 12 includes an opening 16 that enables imaging of a specimen contained in a specimen holder 18 that is positioned on a top surface of the stage. More particularly, the opening 16 provides access for the optical system 14 and, as described below, enables the bottom surface of the specimen holder 18 to contact liquid contained within an optical element of the system.

In the embodiment shown in FIG. 1, the optical system 14 generally includes an excitation branch 20 and a detection branch 22. The optical elements of the excitation branch 20 include a light source 24, an optical density filter 26, a beam expander 28 (which is shown comprising an objective 30 and a lens 32), a cylindrical lens 34, an adjustable slit aperture 36, and an excitation objective 38. By way of example, the light source 24 is a 473 nm or 532 nm diode-pumped solid-state laser (MBL-FN-473-50 mW and MGL-FN-532-500 mW, Changchun New Industries Optoelectronics, China), the objective 30 is a 10× objective (RMS10X, Thorlabs), the lens 32 is a 75 mm lens (AC254-075-A, Thorlabs), the cylindrical lens 34 is a 200 mm focal length cylindrical lens (LJ1653RM-A, Thorlabs), and the excitation objective 38 is a 20×0.42 NA objective with a working distance of 20 mm (Mitutoyo).

The optical elements of the detection branch 22 include a detection objective 40, a tube lens 42, an aberration-correcting cylindrical lens 44, relay lenses 46 and 48, an emission filter 50, and a light sensor 52. By way of example, the detection objective 40 is a 10×0.3 NA objective with a working distance of 15.2 mm (Nikon), the cylindrical lens 44 has focal length of 10 m (SCX-50.8-5000.0, Melles Griot), the relay lens 46 is a 75 mm focal length lens (AC254-075-A-ML, Thorlabs), the relay lens 48 is a 150 mm focal length lens (AC254-150-A-ML, Thorlabs), and the light sensor 52 is an sCMOS camera (Flash 4.0, Hamamatsu). In some embodiments, both the excitation objective 38 and the detection objective 40 are mounted in translation stages (not shown) that can travel approximately ½" along their optical axes. This enables fine alignment of both objectives 38, 40 so that their focal planes overlap.

Also included in the optical system 14 is an open-top, hollow prism 54 that is adapted to contain a clear liquid, such as water. The prism 54 is positioned in the opening 16 of the stage 12 at a position at which its top surface is generally level with the top surface of the stage. In this position, the liquid (e.g., water) contained in the prism 54 can contact the bottom surface of the specimen holder 18 while still enabling the specimen holder 18 to freely translate relative to the prism. The optical elements of the excitation branch 20 and the detection branch 22 are both aligned with the prism 54 such that the optical axes of the excitation objective 38 and the detection objective 40 are perpendicular to angled windows 56 and 58 of the prism, respectively. In some embodiments, these windows 56, 58 comprise glass coverslips through which light can enter and exit the prism 54. In some embodiments, the prism 54 can be mounted to stationary mechanical components that support the excitation objective 38 (not shown) to correctly position the prism relative to the objectives 38, 40 and the stage 12. As shown in FIG. 1, the optical axes of the objectives 38, 40 intersect at a point near (e.g., just above) the top surface of the stage so as to be in a position in which the objectives can focus on a specimen contained in the specimen holder 18.

Figure 2:
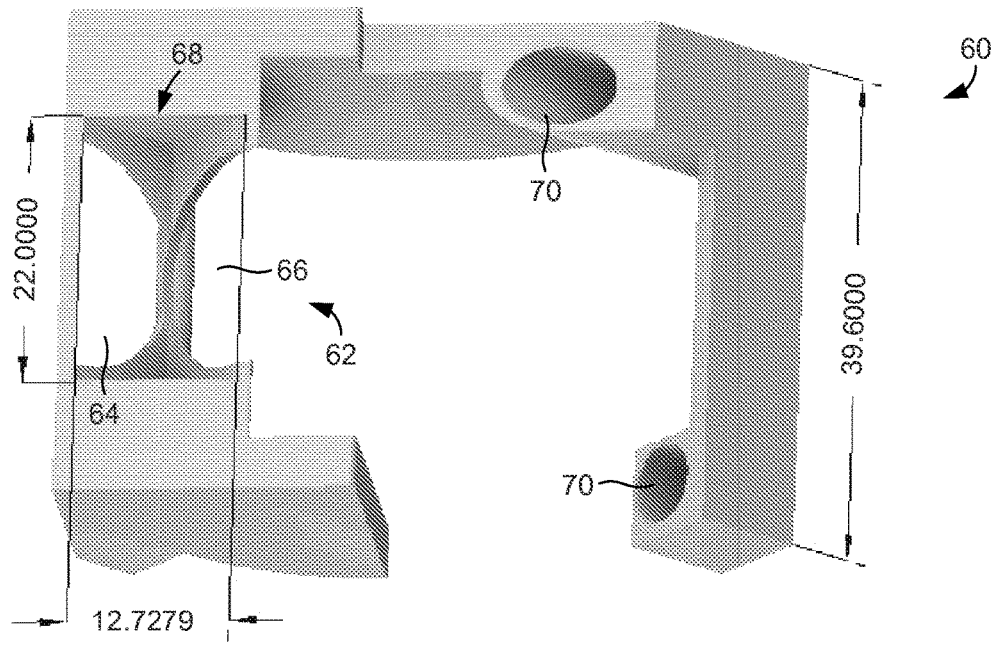
FIG. 2 is a top perspective view of an embodiment of an imaging prism that can be used in the SPIM system of FIG. 1.

FIG. 2 illustrates an example apparatus 60 that includes a prism 62 that was constructed out of three-dimensionally printed acrylonitrile-butadiene-styrene (ABS) plastic (Dimension uPrint). As shown in this figure, the prism 62 is generally hollow and triangular (in cross-section) and includes openings 64 and 66 in which glass coverslips (not shown) can be mounted. By way of example, the coverslips can be approximately 9×18 $mm^2$ coverslips and can be glued to the sides of the prism 62 so that they face the two objectives 38, 40. The top of the prism 62 includes an opening 68 that enables liquid contained in the prism 62 to contact the specimen holder, such as a glass or plastic coverslip-bottomed specimen holder or a microfluidic device. By way of example, the opening 68 is approximately 18×13 mm. As is further shown in FIG. 2, the apparatus 60 includes mounting holes 70 that enable the apparatus to be mounted to another component, such as the stationary mechanical components that support the excitation objective 38. Example dimensions for the apparatus 60 are shown in FIG. 2.

During use of the SPIM system, the excitation objective 38 focuses excitation laser light to a sheet approximately 7 mm past the window 56 of the prism 54 and just above the top surface of the stage 12. The thickness of the light sheet can be approximately 4.2 µm. In some embodiments, the lateral and axial full-widths at half-maximum (FWHMs) of the point spread function (PSF) of the microscope 10 are approximately 1.2 µm and 5.6 µm, respectively. In some embodiments, the power of the excitation light is approximately 120 to 480 µW. Assuming an exposure time of approximately 5 to 20 seconds, the energy delivered to the specimen in one scan can be approximately 2.4 mJ.

Figure 3A:
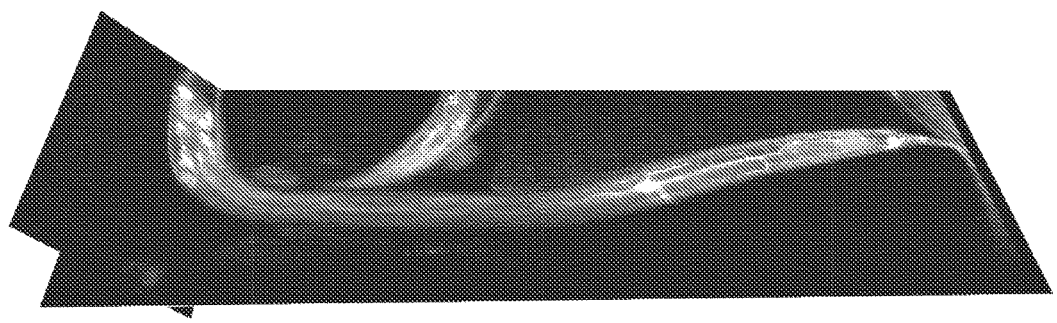
FIG. 3(a) is an image of two slices through volumetric data of C. Elegans with PVD sensory neurons labeled with green fluorescent protein (GFP).
Figure 3B:
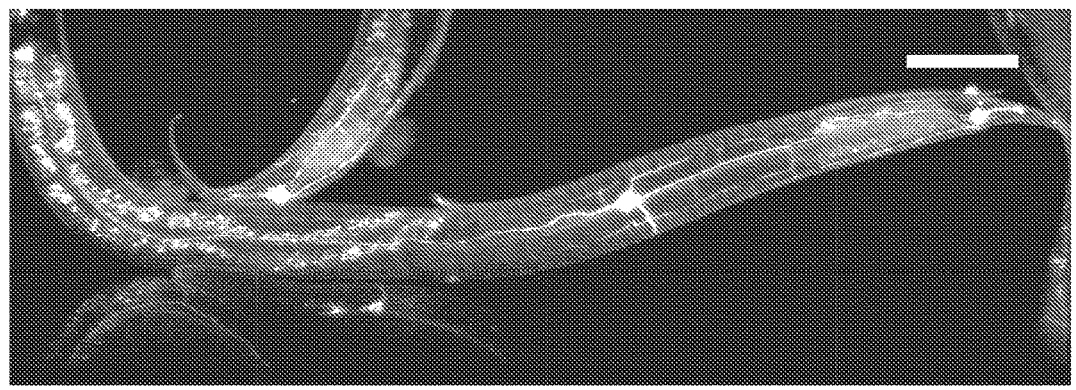
FIG. 3(b) is a z-projection of data shown in FIG. 3(a).

To acquire three-dimensional data, the stage 12 can be scanned with the light sheet and the optical system 14, including the prism, fixed and the light sensor 52 will record slices at a 45° angle relative to the scanning direction. For stationary and slowly moving specimens, the stage 12 can be scanned at a speed of approximately 20 to 100 µm/sec and images can be acquired at a frequency of approximately 20 to 100 Hz. The stack of images captured through this process can then be transformed to generate slices in the x-y plane and z projections, which can be used for three-dimensional reconstruction. FIG. 3 shows an example of such imaging. In particular, shown are images of *Caenorhabditis elegans*, which was confined between a glass slide and a coverslip. FIG. 3(*a*) shows two slices through volumetric data of *C. Elegans* with PVD sensory neurons labeled with green fluorescent protein (GFP). The tilted slice shows the raw camera image prior to any transformation. The other slice is an x-y section. FIG. 3(*b*) shows a z-projection of the data shown in FIG. 3(*a*).

*Drosophila* embryos were imaged using the system described above to evaluate the system's performance. The *Drosophila* expressed membrane-targeted GFP in all neurons (elav-gal4(iii)/UASCD4::tdGFP). Embryos were collected using standard protocols and aged for given hours on grape agar plates at 25° C. The embryos were dechorionated in a solution of 50% bleach before imaging.

Microfluidic devices were fabricated using standard polydimethylsiloxane (PDMS)-based soft lithography techniques. Two-layered master molds were made by spin coating negative photoresist (SU-8, Microchem) that were 30 µm and 200 µm thick, respectively. Devices were cast using a 10:1 PDMS pre-polymer to cross-linker mix (Sylgard 184, Dow Corning). The devices were de-molded and through-holes were created using 1.5 mm and 0.75 mm diameter biopsy punches (Miltex) for embryo loading and liquid loading channels, respectively. The devices were then oxygen plasma treated (Harrick Plasma) and bonded to a glass coverslip (24×30 mm No. 1.5, VWR).

Figure 4:
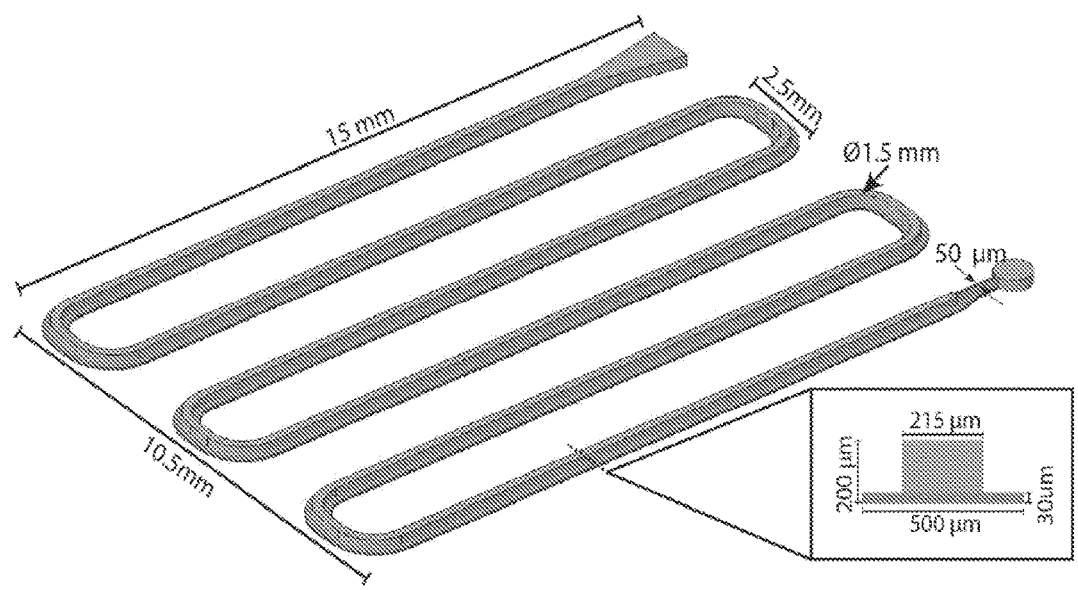
FIG. 4 is a perspective view of a simple microfluidic device for observing the development of many Drosophila embryos.

A simple microfluidic device is shown in FIG. 4. The channel of the device can hold hundreds of embryos but less than 50 *Drosophila* embryos were loaded into the device and the only embryos that were imaged were those that occupied one of the straight 14 mm long sections of the channel. The channel's width and height were 215 µm and 200 µm, respectively, so that the embryos lined up single-file along the channel.

The specimen was moved through the light sheet in the x-direction with the motorized stage to image 32 embryos. The stage was moved at 20 µm/sec and images were recorded at 20 Hz. Later, the stage was moved at 100 µm/sec and images were recorded at 100 Hz to reduce image blur caused by twitching of the embryos. Therefore, it took either 11.5 or 2.3 minutes to image the entire row of embryos. The scans were automatically repeated every 40 minutes for about 12 hours. Because of the long imaging duration, water in the prism would evaporate if no action were taken to prevent this. Therefore, a syringe pump was used to replenish the water at a flow rate of approximately 600 to 1000 µL/hour. Because the bottom side of the microfluidic device was clear of any tubing or obtrusions, it was possible to scan the stage for the entire channel length, capturing three dimensional images of all 32 embryos in a single 0.2×0.22× 14 mm³ volume in as short as 2.3 minutes. The results of this imaging are shown in FIG. 5.

Figure 6:
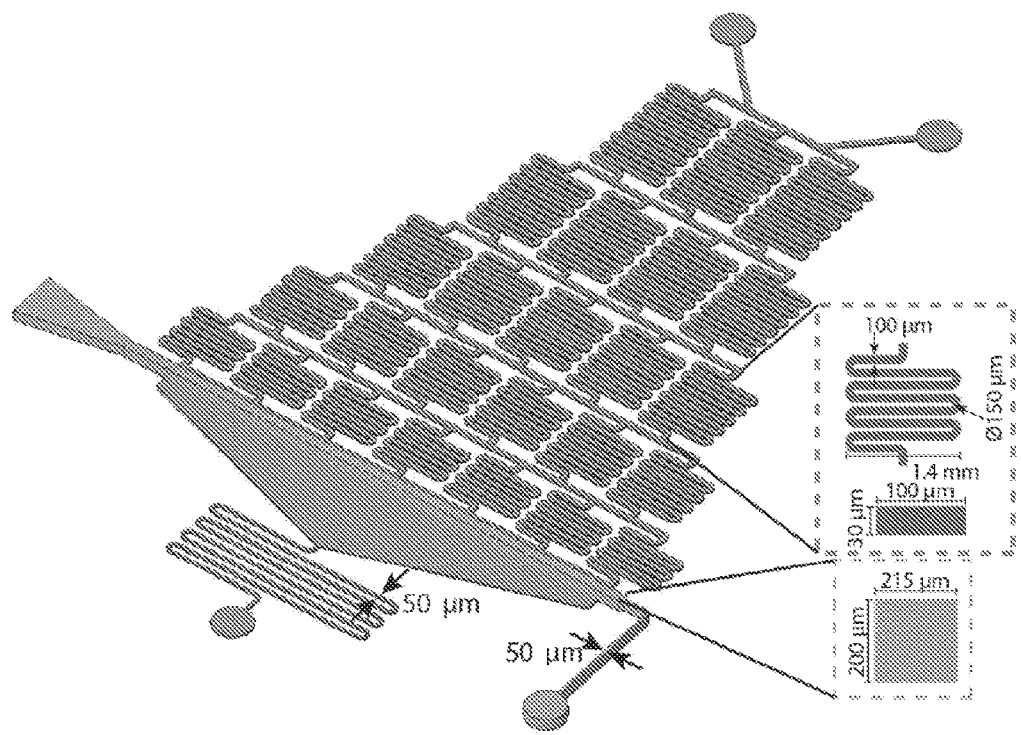
FIG. 6 is a perspective view of a microfluidic device used to establish a chemical gradient along the channel holding Drosophila embryos.

The relatively complex microfluidic device depicted in FIG. 6 was next used with methylmercury chloride, a known teratogen15, to observe the development of *Drosophila* exposed to a chemical gradient. This device comprised a single, straight channel to hold the embryos. A linear concentration gradient ran perpendicular to this channel. In short, a solution of 100% phosphate-buffered saline (PBS) buffer and a solution of 200 µM methylmercury chloride in PBS were flowed into two input valves with syringe pumps and subsequent branches in the device mix to distribute the two solutions. The entire channel containing 32 embryos was automatically imaged about every 20 minutes for over 36 hours. During the imaging, the stage was moved at 80 µm/sec and the camera acquired frames at 80 Hz.

The device maintained a 0 to 200 µM linear gradient of methylmercury chloride along the channel. Developmental disruption due to methylmercury was clearly recorded over 36 hours of imaging: the condensation of the ventral nerve cord that normally occurs at 13 to 16 hours after egg laying (AEL) was observed in only the six embryos at the lowest end of the gradient (see FIG. 7). This experiment demonstrates the power of combining SPIM and microfluidics to observe environmental effects on development.

Figure 8:
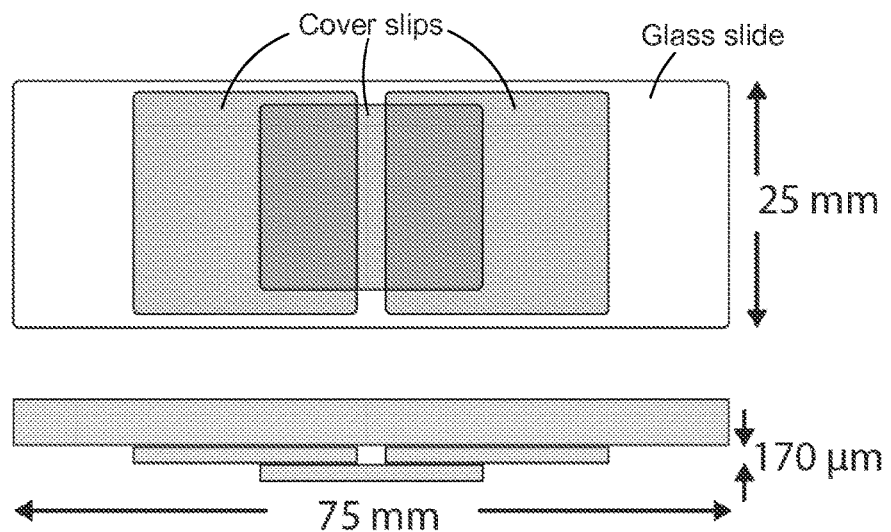
FIG. 8 shows schematic top and side views of a slide and coverslips used to create channel to hold moving Drosophila larvae.
Figure 9A:
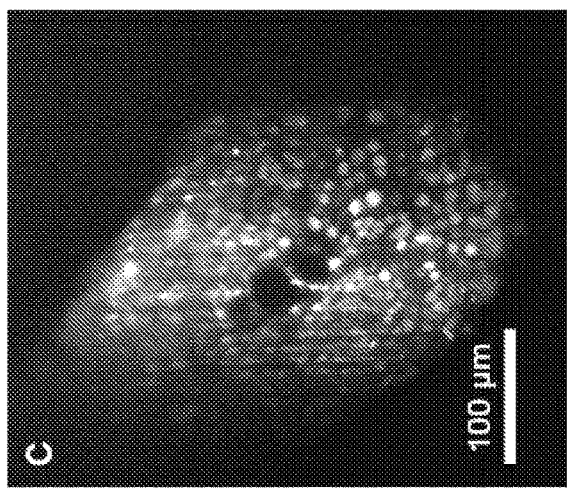
FIG. 9(a) shows one x-y slice of a zebrafish embryo in a 96-well plate. All nuclei are labeled with mRFP.
Figure 9C:
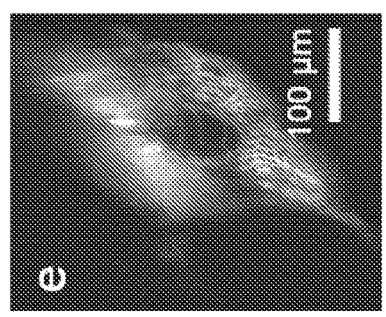
FIG. 9(c) shows an image of the same embryo as recorded on the camera.
Figure 9B:
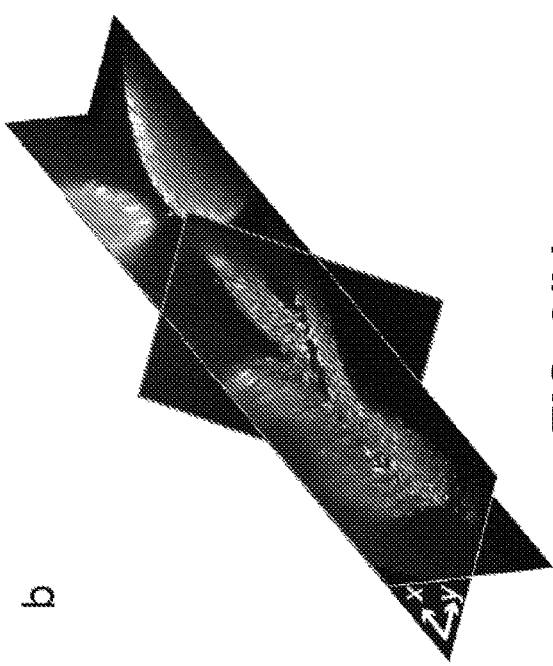
FIG. 9(b) shows multiple slices from the same embryo shown in FIG. 9(a). The tilted slice is the raw camera image before any transformations. The other two slices show an x-y and x-z cut.
Figure 9E:
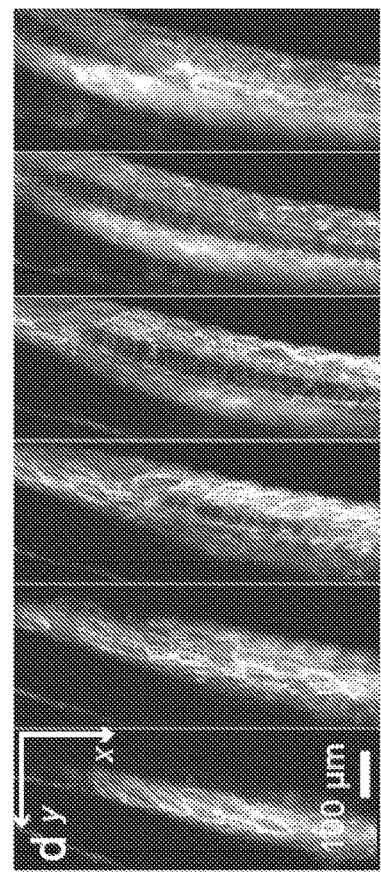
FIG. 9(e) shows an image from data shown in FIG. 5(d) as recorded by the camera.
Figure 9D:
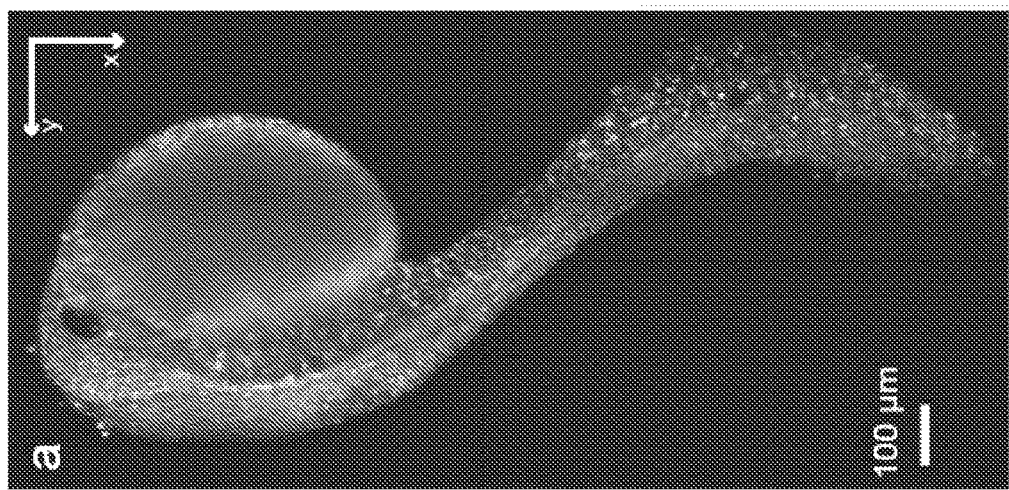
FIG. 9(d) shows six x-y slices through the tail of a zebrafish with tdTomato labeling of the cell membranes.

In addition to microfluidic channels, it was further demonstrated that a SPIM system can image moving first instar larvae (36:00 AEL) of *Drosophila* atop a coverslip. To ensure that the larvae were crawling along the microscope scanning direction, two pieces of coverslips were placed side-by-side on top of another piece of coverslip to form a trough approximately 300 µm wide and 1.5 cm long, as shown in FIG. 8. A glass slide was taped to the top for support. Four larvae with GFP-labeled neurons were trapped in a roughly 1 cm section of the trough. To reduce potential motion blur, a scanning speed of 800 µm/sec (120 Hz camera recording) was used. A time sequence of SPIM images was acquired at 22 sec intervals, as shown in FIG. 9 (the interval can be as short as 1.3 sec if only one larva is imaged). During recording, the larvae exhibited different speeds of movement and even inversion of the moving direction. Combined with genetically encoded calcium sensors, the SPIM system could potentially be used to follow neuronal activity in these freely behaving larvae.

Next, the ability of the SPIM system to image zebrafish embryos in a 96-well plate was tested. Zebrafish were maintained in accordance with National Institutes of Health and University of California San Francisco guidelines. Individual embryos were dechorionated and placed in the wells of a 96-well plate containing Danieau's solution (NaCl 17.4 mM, KCl 0.21 mM, $MgSO_4.7H_2O$ 0.12 mM, $Ca(NO_3)_2$ 0.18 mM, HEPES 1.5 mM). They were cultured at 28° C. The following transgenic lines were established: tg[EF1α-H2BmRFP] (in which the nuclei are fluorescently labeled) and tg[EF1α-myrTdTomato] (in which the cell membranes are fluorescently labeled). H2B-mRFP or myr-Tdtomato were cloned into the transposon vector PT2KXIG, driven by the ubiquitous promoter EF1α, to obtain the DNA plasmids EF1α-H2BmRFP-PT2KXIG and EF1α-myrTdTomato-PT2KXIG. These DNA constructs were microinjected together with tol2 transposase RNA into 1-cell stage wild type (AB) zebrafish embryos.

Forty-eight hour post-fertilized embryos were placed with mRFP tagged nucleus or tdTomato tagged plasma membrane in a glass-bottomed 96-well plate and were allowed to settle to the bottom. The SPIM images clearly resolved the nuclei or the membrane of individual cells throughout the embryo (see FIG. 9). The heartbeat and blood flow in the embryo were recorded using a 60 Hz acquisition at a fixed focal plane. These experiments demonstrate the compatibility of the SPIM system with multiwell plates, which enable the use of SPIM system in high-throughput applications.

Figure 10:
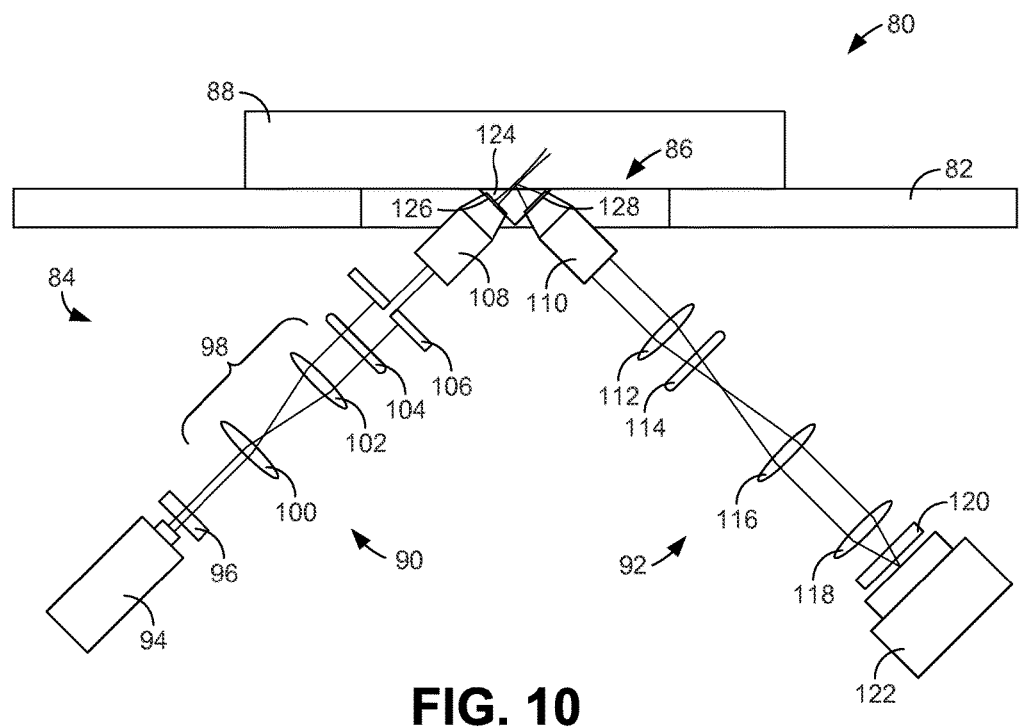
FIG. 10 is a schematic side view of a second embodiment of a SPIM system.

It is noted that the SPIM system described herein uses the simplest method (cylindrical lens) to create the illumination light sheet. Various approaches can be directly applied to the system without any modification to the prism to improve the axial resolution and image quality. These approaches include the generation of a light sheet by scanning a focused laser beam and the use of Bessel beam and the dual-side SPIM configuration to alternatively illuminate and detect fluorescence from both objectives. In addition, the two air objectives can be replaced with water-dipping objectives for higher numerical aperture (NA). FIG. 10 shows an example of such a SPIM microscope 80.

The SPIM system shown in FIG. 10 is similar in many ways to the system shown in FIG. 1. Accordingly, the system comprises a SPIM microscope 80 that includes a motorized stage 82 and a SPIM optical system 84 that is positioned beneath the stage. The stage 82 includes an opening 86 that enables imaging of a specimen contained in a specimen holder 88.

The optical system 84 includes an excitation branch 90 and a detection branch 92. The optical elements of the excitation branch 90 include a light source 94, an optical density filter 96, a beam expander 98 (which is shown comprising an objective 100 and a lens 102), a cylindrical lens 104, an adjustable slit aperture 106, and an excitation objective 108. The optical elements of the detection branch 92 include a detection objective 110, a tube lens 112, an aberration-correcting cylindrical lens 114, relay lenses 116 and 118, an emission filter 120, and a light sensor 122.

Also included in the optical system 84 is an open-top, hollow prism 124 that is adapted to contain a clear liquid, such as water. The prism 124 is positioned in the opening 86 of the stage 82 at a position at which its top surface is generally level with the top surface of the stage so that the liquid (e.g., water) contained in the prism 124 can contact the bottom surface of the specimen holder 88. In the embodiment of FIG. 10, however, the prism 124 has openings 126 and 128 instead of windows and the objectives 108, 110 are dipping (e.g., water-dipping) objectives that extend through the openings such that their tips are immersed in the liquid contained in the prism. Sealing members, such as O-rings, can be used in the openings 126, 128 to seal the objectives 108, 110 to the prism 124 to prevent leaks. In some embodiments, the objectives are 20×0.8 NA objectives.

Figure 11:
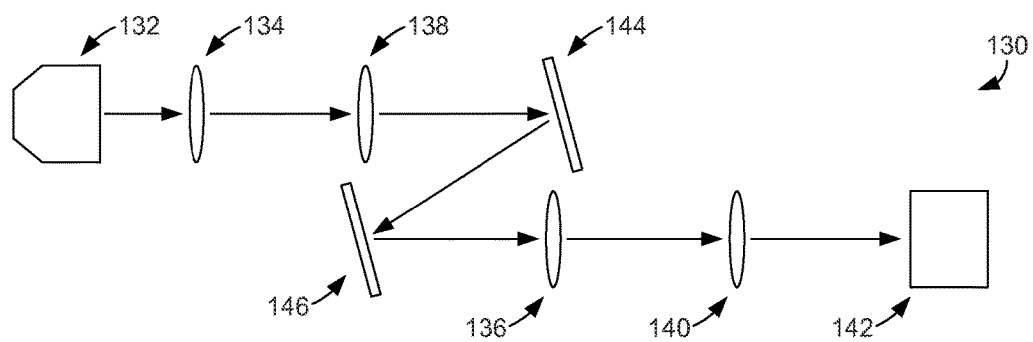
FIG. 11 is a schematic side view of an alternative detection branch that can be incorporated into the SPIM system of FIG. 10.

As is apparent from the above discussion, the objectives of FIG. 10 can have higher NAs than the objectives of FIG. 1. While higher NA objectives provide higher spatial resolution and therefore enable imaging of subcellular structures, they also tend to increase aberration. In some embodiments, the SPIM system can further comprise components that correct such aberration. FIG. 11 shows an alternative detection branch 130 that can be incorporated into the optical system 84 in place of the detection branch 92 shown in FIG. 10 to correct aberration. As with the detection branch 92, the detection branch 130 includes a detection objective 132, a tube lens 134, a cylindrical lens 136, relay lenses 138 and 140, and a light sensor 142. In addition, however, the detection branch 130 includes an adaptive optics element 144, such as a deformable mirror or a spatial light modulator (SLM), which can be used to compensate for the aberration created by the detection objective 132. Also shown in FIG. 11 is a mirror 146 that can be used, if necessary, to direct light from the adaptive optics element 144 along the optical path of the detection branch 130 to the light sensor 142.

The adaptive optics element 144 can be calibrated using a calibration process. In this process, objects, such as fluorescent beads, can be provided in the specimen holder and a PSF of images of the objects can be acquired. The PSF extracts the aberration and phase retrieval can be performed on the PSF to obtain the pupil function. The pupil function can be unwrapped to obtain the necessary phase correction, which can then be applied to the adaptive optics element 144. In some embodiments, this procedure can then be repeated, either for a fixed number of iterations or until convergence is received, to increase the accuracy of the calibration.

The invention claimed is:

1. A selective plane illumination microscopy system for capturing light emitted by an illuminated specimen, the system comprising:
    a specimen stage having a top surface adapted to support a specimen holder and an opening adapted to provide access to a bottom of the holder; and
    a selective plane illumination microscopy optical system positioned beneath the stage, the optical system configured to illuminate the specimen with a sheet of excitation light and including an excitation objective, a detection objective, and an open-top, hollow prism that is adapted to contain a liquid, wherein the prism is positioned within the opening of the stage and optical axes of the objectives are aligned with the prism such that the axes pass through the prism and intersect at a position near the top surface of the specimen stage.

2. The system of claim 1, wherein the stage is motorized so as to be capable of being scanned in x and y directions.

3. The system of claim 1, wherein the optical axes of the excitation and detection objectives form an angle of approximately 45 degrees with the open top of the prism and form an angle of approximately 90 degrees with each other.

4. The system of claim 1, wherein prism is positioned within the opening of the stage such that a top surface of the prism is generally level with the top surface of the stage so that the liquid contacts the bottom of the specimen holder when the prism is filled with the liquid.

5. The system of claim 1, wherein the prism comprises windows through which light from the optical system enters and exits the prism when the system is operated.

6. The system of claim 5, wherein the excitation and detection objectives are air objectives positioned outside of the prism.

7. The system of claim 1, wherein the prism comprises openings through which light from the optical system enters and exits the prism when the system is operated.

8. The system of claim 7, wherein the excitation and detection objectives are dipping objectives positioned in the openings such that they are immersed in the liquid when the prism is filled with the liquid.

9. The system of claim 8, wherein the optical system further comprises an adaptive optics element configured to compensate for aberration created by the detection objective.

10. The system of claim 9, wherein the adaptive optics element comprises a deformable mirror.

11. The system of claim 9, wherein the adaptive optics element comprises a spatial light modulator.

12. The system of claim 1, wherein the optical system further comprises a cylindrical lens that forms a sheet of excitation light that is focused by the excitation objective to be coincident with the specimen and a focal plane of the detection objective.

13. The system of claim 1, wherein the optical system further comprises a laser that generates the light.

14. The system of claim 1, further comprising a light sensor that receives fluorescence emitted from the specimen.

15. An imaging prism for use in an opening provided within a microscope stage, the prism comprising:
    a body having a generally triangular cross-section that defines a hollow space;

angled lower sides through which light can enter and exit the prism, the sides comprising openings through which the light passes; and an open top adapted to be positioned level with a top surface of the microscope stage;

wherein the prism is configured to be filled with a liquid such that a top surface of the liquid is positioned so as to contact a bottom surface of a specimen holder supported on top of the microscope stage.

16. The imaging prism of claim 15, wherein windows are positioned within the openings to seal the openings.

17. A method for performing selective plane illumination microscopy on a specimen, the method comprising:

positioning an open-top, hollow prism adapted to contain a liquid in an opening formed in a microscope stage, wherein the prism is positioned such that its open top is generally level with a top surface of the stage;

positioning an excitation objective and an detection objective of a selective plane illumination microscopy optical system below the stage such that the optical axes of the objectives pass through the prism and intersect at a position near the top surface of the specimen stage;

illuminating the specimen contained in a specimen holder supported on the top surface of the stage with a sheet of laser light focused by the excitation objective; and capturing light emitted by the specimen that passes through the detection objective.

18. The method of claim 17, wherein positioning an excitation objective and a detection objective comprises positioning the objectives outside of the prism such that they are not immersed in the liquid.

19. The method of claim 17, wherein positioning an excitation objective and a detection objective comprises positioning the objectives inside of the prism such that they are immersed in the liquid.

* * * * *